US009821300B2

(12) United States Patent
Coelho Tsou et al.

(10) Patent No.: US 9,821,300 B2
(45) Date of Patent: Nov. 21, 2017

(54) PROCESS FOR PRODUCING AN SI-BONDED FLUIDIZED-BED CATALYST

(71) Applicant: BASF SE, Ludwigshafen (DE)

(72) Inventors: Joana Coelho Tsou, Heidelberg (DE); Sebastian Ahrens, Wiesloch (DE); Christian Schneider, Mannheim (DE); Thomas Heidemann, Viernheim (DE); Bilge Yilmaz, Mannheim (DE); Robert Bayer, Sinsheim (DE); Michael Schlei, Limburgerhof (DE); Sebastian Kranz, Hassloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/272,082

(22) Filed: Sep. 21, 2016

(65) Prior Publication Data
US 2017/0007989 A1    Jan. 12, 2017

Related U.S. Application Data

(62) Division of application No. 13/500,966, filed as application No. PCT/EP2010/064876 on Oct. 6, 2010, now Pat. No. 9,486,796.

(30) Foreign Application Priority Data

Oct. 8, 2009 (EP) .................................... 09172603

(51) Int. Cl.
| | | |
|---|---|---|
| *B01J 29/06* | (2006.01) | |
| *C07C 15/04* | (2006.01) | |
| *B01J 29/48* | (2006.01) | |
| *C07C 5/41* | (2006.01) | |
| *C07C 2/82* | (2006.01) | |
| *C07C 2/84* | (2006.01) | |
| *B01J 29/068* | (2006.01) | |
| *B01J 29/076* | (2006.01) | |
| *B01J 29/44* | (2006.01) | |
| *B01J 29/74* | (2006.01) | |
| *B01J 29/78* | (2006.01) | |
| *C07C 2/76* | (2006.01) | |
| *B01J 37/08* | (2006.01) | |
| *B01J 37/00* | (2006.01) | |

(52) U.S. Cl.
CPC ............... *B01J 29/48* (2013.01); *B01J 29/06* (2013.01); *B01J 29/068* (2013.01); *B01J 29/076* (2013.01); *B01J 29/44* (2013.01); *B01J 29/7476* (2013.01); *B01J 29/7876* (2013.01); *B01J 37/0045* (2013.01); *B01J 37/08* (2013.01); *C07C 2/76* (2013.01); *C07C 2/82* (2013.01); *C07C 2/84* (2013.01); *C07C 5/41* (2013.01); *C07C 5/412* (2013.01); *C07C 5/415* (2013.01); *C07C 15/04* (2013.01); *B01J 37/0036* (2013.01); *B01J 2229/20* (2013.01); *B01J 2229/32* (2013.01); *B01J 2229/42* (2013.01); *C07C 2523/755* (2013.01); *C07C 2529/48* (2013.01); *C07C 2531/02* (2013.01); *Y02P 20/52* (2015.11)

(58) Field of Classification Search
CPC ........ B01J 29/44; B01J 29/48; B01J 2229/20; B01J 2229/32; B01J 2229/42; B01J 37/0036; B01J 37/0045; B01J 29/7476; B01J 29/7876; C07C 2529/40; C07C 2529/44; C07C 2529/48; C07C 2/76; C07C 2/82; C07C 15/04; C07C 5/41; C07C 5/412; C07C 5/415
USPC .......... 502/8, 9, 60, 63, 64, 66; 585/446, 467
See application file for complete search history.

(56) References Cited

U.S. PATENT DOCUMENTS

| | | | |
|---|---|---|---|
| 5,352,645 A | 10/1994 | Schwartz | |
| 5,492,883 A | 2/1996 | Wu | |
| 5,633,217 A * | 5/1997 | Lynn | ..................... B01J 20/183 502/159 |
| 6,114,268 A | 9/2000 | Wu et al. | |
| 6,235,955 B1 | 5/2001 | Ya et al. | |
| 7,582,583 B2 | 9/2009 | Bosch et al. | |
| 8,278,237 B2 | 10/2012 | Yamada et al. | |

(Continued)

FOREIGN PATENT DOCUMENTS

| | | |
|---|---|---|
| DE | 198 26 209 | 12/1999 |
| JP | 2008-502563 A | 1/2008 |

(Continued)

OTHER PUBLICATIONS

Office Action dated Jul. 1, 2013 in Japanese Patent Application No. 2012-532574 submitting English translation only.

(Continued)

*Primary Examiner* — Elizabeth Wood
(74) *Attorney, Agent, or Firm* — Oblon, McClelland, Maier & Neustadt, L.L.P.

(57) ABSTRACT

The invention relates to a process for producing a particulate, Si-bonded fluidized-bed catalyst having improved abrasion resistance, which comprises the steps I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying, and
IV. calcination of the spray-dried fluidized-bed catalyst obtained from step III, and an Si-bonded fluidized-bed catalyst which can be produced by this process and also its use for the nonoxidative dehydroaromatization of $C_1$-$C_4$-aliphatics.

9 Claims, No Drawings

(56) References Cited

U.S. PATENT DOCUMENTS

| | | |
|---|---|---|
| 2003/0141252 A1 | 7/2003 | Okamoto et al. |
| 2004/0167342 A1* | 8/2004 | Strebelle .......... B01J 29/89 549/533 |
| 2006/0199730 A1 | 9/2006 | Seely et al. |
| 2008/0021251 A1 | 1/2008 | Laccino et al. |
| 2008/0033212 A1 | 2/2008 | Bosch et al. |
| 2008/0221326 A1 | 9/2008 | Bosch et al. |
| 2010/0312031 A1 | 12/2010 | Heidemann |
| 2011/0060176 A1 | 3/2011 | Kiesslich et al. |
| 2011/0124933 A1 | 5/2011 | Kiesslich et al. |
| 2011/0301398 A1 | 12/2011 | Heidemann et al. |
| 2012/0022310 A1 | 1/2012 | Schneider et al. |

FOREIGN PATENT DOCUMENTS

| | | |
|---|---|---|
| JP | 2008-502637 A | 1/2008 |
| JP | 2009-28710 A | 2/2009 |
| WO | 02 070123 | 9/2002 |
| WO | 2005 032713 | 4/2005 |
| WO | 2005 123256 | 12/2005 |
| WO | 2005 123658 | 12/2005 |
| WO | 2009 004843 | 1/2009 |
| WO | 2009 124902 | 10/2009 |

OTHER PUBLICATIONS

Qun Dong, et al., "Studies on Mo/HZSM-5 Complex Catalyst for Methane Aromatization", Journal of Natural Gas Chemistry, vol. 13, 2004, pp. 36-40.

English translation of Abstract for Matus E.V. Sintez I issledovanie Mo/ZSM-5 katalizatorov degidroaromatizatsii metana ("Synthese und Untersuching von Mo/ZMS-5 Methan-Dehydroaromatisierungs-Katalysatoren") Dissertation, Novosibirsk, Oct. 2007, 158 Seiten Zusammenfassung http://www.dissercat.com/content/sintez-i-issledovanie-mozsm-5-katalizatorov-degidroaromatizatsii-metana.

German translation Office Action dated Oct. 18, 2013 in European Patent Application No. 201270529.

International Search Report dated Dec. 23, 2010 in PCT/EP10/64876 Filed Oct. 6, 2010.

* cited by examiner

PROCESS FOR PRODUCING AN SI-BONDED FLUIDIZED-BED CATALYST

CROSS-REFERENCE TO RELATED APPLICATION(S)

This application is a divisional application of U.S. application Ser. No. 13/500,966, filed on Apr. 9, 2012, which is a national stage entry application of PCT/EP10/064876, filed on Oct. 6, 2010, the text of which is incorporated by reference, and claims the benefit of priority from European Patent Application No. 09172603.4, filed on Oct. 8, 2009, the entire contents of which are incorporated herein by reference.

DESCRIPTION

The invention relates to a process for producing a particulate, Si-bonded fluidized-bed catalyst having improved abrasion resistance, which comprises the steps I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying, and
IV. calcination of the spray-dried fluidized-bed catalyst obtained from step III, and an Si-bonded fluidized-bed catalyst which can be produced by this process and also its use for the nonoxidative dehydroaromatization of $C_1$-$C_4$-aliphatics.

For many solid-catalyzed reactions in which the starting materials and the products are present in the gas phase, it has been found to be advantageous to cavy out the reaction in a fluidized catalyst bed. The catalyst is in this case present in particulate form. The advantages of a fluidized bed are, inter alia, the relatively easy handling and solids transport of the fluidized catalyst bed, the uniform temperature distribution and the good heat exchange due to the intensive mixing of the catalyst particles by the fluidization and also the relatively large gas-solid interface due to the small particle size of the catalyst.

The catalyst particles in a fluidized bed are subject to large forces due to impacts with other catalyst particles and with the wall and these can lead to breaking of the catalyst particles and to abrasion of small particles from the catalyst surface. The small particles can be discharged from the reactor with the gas phase and have to be separated off from the reactor output, which costs money. The catalyst lost by discharge from the reactor has to be replaced. The breaking and the abrasion of small particles significantly reduce the operating life of the catalyst particles in the fluidized bed. Catalysts which are to be used as fluidized-bed catalysts therefore have to display a high abrasion resistance.

Carrying out the reaction in a circulating fluidized bed is particularly useful for the nonoxidative dehydroaromatization of methane and higher aliphatics, hereinafter also referred to as DHAM. Furthermore, it is known from WO 2005/032713 that the presence of an Si-comprising binder has a positive effect on the DHAM.

Various methods are already known for increasing the abrasion resistance of catalyst particles comprising Si-comprising binders.

WO 02/070123 describes spherical abrasion-resistant particles which have a particle size of from 20 to 120 µm and are produced by spray drying a suspension comprising an inorganic sol, an inorganic particulate material which is not a metal sol and an abrasion modifier. As abrasion modifiers, preference is given to using particles which are obtained in the production of spherical particles and are not suitable as fluidized-bed catalysts. As inorganic sol, preference is given to using silica sol.

According to US 2006/0199730, a mixture of silica sols with silica particles having two different average particle sizes is used. The mixture of relatively large and relatively small particles is said to ensure better packing of the silica particles and give a higher density.

U.S. Pat. No. 5,352,645 relates to the production of abrasion-resistant, spherical silica particles having a particle size of from 1 to 50 µm by spray drying a suspension composed of silica sol and an additive selected from among urea and ammonium citrate.

Despite the possibilities described in the prior art for producing abrasion-resistant, Si-bonded fluidized-bed catalysts, there is a need for Si-bonded fluidized-bed catalysts which have an improved abrasion resistance compared to the previously known catalysts, in particular abrasion-resistant fluidized-bed catalysts which are suitable for the nonoxidative dehydroaromatization of methane and higher aliphatics.

This object is achieved by the process of the invention for producing an Si-bonded fluidized-bed catalyst, which comprises the steps I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying, and
IV. calcination of the spray-dried fluidized-bed catalyst obtained from step III, and also the particulate, Si-bonded fluidized-bed catalyst which can be produced by the process of the invention.

In the process of the invention, catalyst particles having the average particle sizes of from 10 to 200 µm which are suitable for operation as fluidized bed are obtained. The catalyst particles obtained by spray drying are essentially spherical, which has a positive effect on the abrasion resistance of the particles.

The catalyst particles according to the invention surprisingly have a higher abrasion resistance than zeolite particles produced by spray drying using other Si-comprising binders such as silica suspensions or colloidal silica. In addition, it has likewise surprisingly been found that the catalyst particles according to the invention have, in contrast to, for example, catalyst particles bound by means of colloidal silica, a higher abrasion resistance at a relatively low binder content than at higher binder contents. This has, in particular, the advantage that the catalysts of the invention comprise, at an improved abrasion resistance, a higher content of catalytically active zeolite than catalysts having a higher binder content. Even when the silicone resin mixtures and further Si-comprising binders such as colloidal silica are used jointly in the process of the invention, catalyst particles which display significantly improved degrees of abrasion are obtained. Catalyst particles produced in this way can even exceed the properties of catalyst particles produced using only silicone resin mixture as binder.

The catalysts produced according to the invention are, in particular, suitable for use in the nonoxidative dehydroaromatization of methane; for example, catalysts according to the invention comprising HZSM-5 as zeolite and molybdenum as active metal display improved yields and selectivities compared to catalysts which likewise comprise HZSM-5 and molybdenum but have been produced using another Si-comprising binder.

The invention is described in detail below.

In step I of the process of the invention, an aqueous suspension of zeolite particles is provided. The zeolite particles can have a desired particle size from the beginning in the provision of the aqueous suspension comprising zeolite particles, but it is also possible to carry out step (Ia) wet milling of the aqueous suspension comprising zeolite particles between provision of the aqueous suspension comprising zeolite particles in step I and addition of the silicone resin mixture in step II.

The zeolite particles in the aqueous suspension preferably have a $D_{90}$ of ≤10 μm, preferably ≤5 μm and particularly preferably ≤3 μm, determined using a Malvern instrument (Malvern Mastersizer 2000). The $D_{90}$ denotes, in the context of a particle size distribution, the particle size at which 90% of the particles have a diameter of ≤$D_{90}$. According to the invention, the particle size of the zeolite particles is selected so as to be sufficiently large to avoid flocculation of the zeolite particles in the aqueous suspension. The zeolite particles are particularly preferably as small as possible but still form a stable suspension.

The concentration of the zeolite particles in the aqueous suspension is usually from 5 to 70% by weight, preferably from 40 to 60% by weight, based on the total weight of the suspension.

The zeolites to be used according to the invention are aluminum silicates which are usually obtained in the sodium form in their preparation. In the Na form, the excess negative charge present in the crystal lattice because of the replacement of 4-valent Si atoms by 3-valent Al atoms is balanced by Na ions. Instead of sodium alone, the zeolite can also comprise further alkali metal and/or alkaline earth metal ions to balance the charge. According to the invention, the at least one zeolite comprised in the catalysts preferably has a structure selected from among the structure types Pentasil and MWW and particularly preferably from among the structure types MFI, MEL, mixed structures of MFI and MEL and MWW. Very particular preference is given to using a zeolite of the ZSM-5 or MCM-22 type. The names of the structure types of the zeolites correspond to the information given in W. M. Meier, D. H. Olson and Ch. Baerlocher, "Atlas of Zeolite Structure Types", Elsevier, 3rd edition, Amsterdam 2001. The synthesis of the zeolites is known to those skilled in the art and can be carried out, for example, from alkali metal aluminate, alkali metal silicate and amorphous $SiO_2$ under hydrothermal conditions. Here, the type of channel system formed in the zeolite can be controlled via organic template molecules, via the temperature and via further experimental parameters.

The aqueous suspension in step I can comprise further auxiliaries suitable for producing a stable suspension having a homogeneous distribution of zeolite particles.

In step II of the process of the invention, a silicone resin mixture comprising one or more hydrolyzable silicone resin precondensates is added. For the purposes of the present invention, "hydrolyzable" means that an OH group is formed in the silicone resin precondensate by contact with water and/or a catalyst as a result of elimination of a group and this OH group can undergo a condensation reaction with further OH groups. Ongoing hydrolysis and condensation reactions lead to formation of the crosslinked silicone resin.

Preference is given to using hydroxyl- and alkoxy-functionalized silicone resin precondensates which have, for example, the following formula

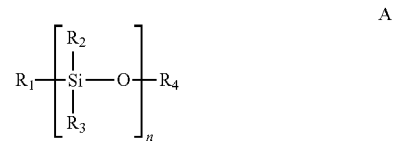

where
$R_1$, $R_2$ and $R_3$: OH, $C_1$-$C_6$-alkoxy, $C_1$-$C_6$-alkyl and $C_6$-$C_9$-aryl,
$R_4$: H, $C_1$-$C_6$-alkyl and $C_6$-$C_9$-aryl and
n: is selected so that the weight average molecular weight of the silicone resin precondensate is from 100 to 10 000 g/mol,
and also mixtures thereof.

According to the invention, particular preference is given to using alkylalkoxysiloxanes having from 1 to 6 carbon atoms, very particularly preferably alkylalkoxysiloxanes having from 1 to 4 carbon atoms and in particular methylmethoxysiloxane, as can be obtained under the trade name Silres® MSE-100 from Wacker Silikon.

The silicone resin precondensates usually comprise mixtures of silicone resin precondensates having different degrees of polymerization and molecular weights, so that the silicone resin precondensates can comprise monomers, oligomers, polymers and mixtures thereof. Thus, according to the invention, the term methylmethoxysiloxane refers to monomethylmethoxysiloxane, oligomethylmethoxysiloxane, polymethylmethoxysiloxane and mixtures thereof.

The silicone resin mixture usually comprises from 10 to 95% by weight, based on the silicone resin mixture, of silicone resin precondensate.

The silicone resin mixture can comprise further constituents in addition to the hydrolyzable silicone resin precondensate. For example, the silicone resin mixture frequently comprises the alcohol formed in the hydrolysis of the alkoxy-functionalized silicone resin precondensates, for example methanol in the case of methylmethoxysiloxane. Furthermore, the silicone resin mixture can comprise a catalyst for the crosslinking reaction.

According to the invention, the silicone resin mixture preferably additionally comprises at least one solvent having a boiling point higher than that of water, for example benzene, toluene, o-xylene, m-xylene, p-xylene and mixtures thereof, particularly preferably toluene. The solvent having the boiling point higher than water evaporates later during spray drying, presumably only after the particles which form during spray drying have been formed. The delayed evaporation of the solvent having a boiling point higher than that of water enables additional pores to be formed in the particles formed during spray drying, and these pores have a positive effect on the suitability of the particles as catalyst. The at least one solvent having a boiling point higher than that of water is preferably present in the silicone resin mixture in a concentration of ≥0.1% by weight, particularly preferably ≥1% by weight, based on the silicone resin mixture.

The silicone resin mixture can additionally comprise components known to those skilled in the art, in particular further Si-comprising binders such as colloidal silica, silica suspensions and silica sols. These further Si-comprising binders can also be added separately from the silicone resin mixture to the zeolite in step II, for example simultaneously from different stock vessels or else successively over time. According to the invention, preference is given to using at least one further Si-comprising binder in step II, with the Si-comprising binder preferably being selected from among colloidal silica, silica suspensions and silica sols. Particular preference is given to at least one further Si-comprising binder being comprised in the silicone resin mixture used in step II, i.e. mixed with the silicone resin mixture before the addition.

When one or more further Si-comprising binders are used in step II, the ratio of silicone resin or silicone resin precondensate to further Si-comprising binder is preferably from 5 to 99% by weight of silicone resin/silicone resin precondensate to from 1 to 95% by weight of further Si-comprising binder, particularly preferably from 10 to 95% by weight of silicone resin/silicone resin precondensate to from 5 to 90% by weight of further Si-comprising binder and very particularly preferably from 15 to 90% by weight of silicone resin/silicone resin precondensate to from 10 to 85% by weight of further Si-comprising binder, based on the sum of the weight of silicone resin or silicone resin precondensate and Si-comprising binder, in each case based on the solids content. The ratio of silicone resin/silicone resin precondensate to Si-comprising binder is very particularly preferably from 75 to 85% by weight of silicone resin/silicone resin precondensate to from 15 to 25% by weight of further Si-comprising binder. The total amount of binders used in step II is selected so that, as described above for the silicone resins/silicone resin precondensates, the total amount of silicone resin/silicone resin precondensate and further Si-containing binders are used instead of the amounts of silicone resin/silicone resin precondensate.

The further Si-comprising binder or binders can be mixed with the silicone resin/silicone resin precondensate before addition of the mixture comprising silicone resin to the zeolite, but it is also possible to add one or further Si-comprising binders separately from the mixture comprising silicone resin in step II, for example simultaneously but also successively.

On addition of the silicone resin mixture to the aqueous suspension of zeolite particles, part of the ester groups comprised in the silicone resin precondensate are hydrolyzed to hydroxyl groups and undergo condensation reactions with further hydroxyl groups. This forms the fully condensed silicone resin. Step II gives an at least two-phase mixture comprising zeolite particles, fully condensed silicone resin, water, alcohol eliminated from the silicone resin precondensate, for example methanol in the case of methoxy-functionalized silicone resin precondensate, and further components originally present in the aqueous suspension of the silicone resin mixture.

The total multiphase mixture obtained in step II is spray dried in step III. During spray drying, the mixture/suspension comprising the zeolite particles and silicone resin is continuously sprayed via nozzles, atomizer discs or other suitable atomization devices (cf., for example, the publication by Arthur Lefebvre, "Atomisation and Sprays", Hemisphere Publishing Corporation, 1989, ISBN 0-89116-603-3) into a drying chamber heated, for example, by means of hot air. Comprehensive information on spray drying may be found, for example, in the publication by K. Masters, "Spray Drying Handbook", Longman Scientific & Technical, 1991, ISBN 0-582-06266-7. During spraying, high shear forces act on the mixture. This results in formation of very small droplets which dry quickly in the heated chamber. The particle size distribution, residual moisture content and morphology of the solid can be adjusted as a function of the type of atomization device used, the spraying pressure, the concentration of the suspension, the drying temperature and the drying rate. The drying temperatures are, for example, in the range from 60° C. to 450° C., and are preferably from 80° C. to 350° C. The particles produced by spray drying are essentially spherical.

The mixture obtained from step II is, according to the invention, homogenized immediately before spraying, so that the constituents of the mixture, in particular the zeolite particles and the fully condensed silicone resin, are very uniformly distributed during spray drying. This can be achieved, for example, by stirring the mixture. It has been found that when toluene-comprising methylmethoxysiloxane is used, the removal of the organic phase leads to catalyst particles which have poorer properties than catalyst particles in which the organic phase has not been separated off before spray drying.

According to the invention, spray drying is followed in step IV by calcination of the spray-dried particulate fluidized-bed catalyst obtained from step III. The catalyst particles obtained during spray drying are usually calcined at temperatures of from 400 to 1200° C., preferably from 500 to 1000° C. and particularly preferably from 700 to 900° C.

Calcination can be carried out under any suitable gas atmosphere, with air and/or lean air being preferred. Furthermore, the calcination is preferably carried out in a muffle furnace, a rotary tube furnace and/or a tunnel kiln, with the calcination time generally being 1 hour or more, for example in the range from 1 to 24 hours or in the range from 3 to 12 hours.

The catalyst particles can be subjected to a further drying step, known as after-drying, between the spray drying of step III and the calcination in step IV.

In a preferred embodiment of the invention, the zeolite particles are subjected to a double ammonium exchange comprising the steps i) ammonium exchange by treatment with an $NH_4$-comprising mixture,
ii) drying and calcination of the zeolite particles,
iii) second ammonium exchange by treatment with an $NH_4$-comprising mixture and
iv) optionally drying and/or optionally calcination of the zeolite particles before step I.

The $NH_4$-comprising mixture usually comprises an ammonium salt selected from the group consisting of ammonium chloride, ammonium carbonate, ammonium hydrogencarbonate, ammonium nitrate, ammonium phosphate, ammonium hydrogenphosphate, ammonium dihydrogenphosphate, ammonium sulfate, ammonium acetate and ammonium hydrogensulfate, preferably ammonium nitrate. Preference is given to using solutions of the ammonium salts as $NH_4$-comprising mixture.

The treatment of the zeolite with the $NH_4$-comprising mixture in steps i) and iii) is carried out by the known methods which are suitable for ammonium exchange of zeolites. These include, for example, steeping, dipping or spraying of the zeolite with an ammonium salt solution, with the solution generally being employed in excess. As solvent, preference is given to using water or alcohols. The solution usually comprises from 1 to 20% by weight of the $NH_4$ component used. The treatment with the $NH_4$-comprising mixture is usually carried out over a period of a number of hours and at elevated temperatures. After the $NH_4$-comprising mixture has acted on the zeolite, excess mixture can be removed and the zeolite can be washed.

In steps ii) and iv), the zeolite is dried at from 40 to 150° C. for a number of hours, usually from 4 to 20 hours. This is followed by calcination of the zeolite at temperatures of from 300 to 700° C., preferably from 350 to 650° C. and particularly preferably from 500 to 600° C. The calcination time is usually from 2 to 24 hours, preferably from 3 to 10 hours and particularly preferably from 4 to 6 hours.

Commercially available zeolites in the H form usually have already gone through a first ammonium exchange by treatment with an $NH_4$-comprising mixture and subsequent drying and calcination, i.e. steps i) and ii) have already been carried out by the manufacture of the zeolite. Commercially procured zeolites which are present in the H form can therefore, according to the invention, be used directly in step iii) of the process of the invention.

The renewed ammonium exchange serves, according to the invention, not only to ensure very complete replacement of the alkali metal and/or alkaline earth metal ions by protons but also brings about structural changes in the zeolite. Thus, the renewed treatment of the zeolite increases, for example, the Si:Al ratio, which is associated with a change in the ratio of the Lewis-acid sites to Brönsted-acid sites. The increase in the Si:Al ratio is caused by dealumination of the zeolite. Another example of the changes in the zeolite caused by the renewed treatment is the increase in the BET surface area.

The zeolite particles obtained after the double ammonium exchange are subsequently used in step I of the process of the invention.

In a further preferred embodiment, step IV is followed by a step

V application of at least one active metal to the particulate fluidized-bed catalyst obtained from step IV and subsequently optionally drying and/or optionally calcination of the particulate fluidized-bed catalyst.

In this embodiment, the process of the invention comprises the steps

I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying,
IV. calcination of the spray-dried fluidized-bed catalyst obtained from step III, and
V. application of at least one active metal to the fluidized-bed catalyst obtained from step IV and subsequently optionally drying and/or optionally calcination of the fluidized-bed catalyst, where steps Ia and i) to iv) as described above can optionally be carried out in addition.

The active metal or metals can, according to the invention, be applied by wet chemical or dry chemical means in step V to the catalyst particles obtained from step IV.

In a wet chemical method, the at least one active component is applied in the form of aqueous, organic or organic-aqueous solutions of its salts or complexes by impregnating the zeolite with the corresponding solution. Supercritical $CO_2$ can also serve as solvent. The impregnation can be carried out by the incipient wetness method in which the porous volume of the zeolite is filled with an approximately equal volume of impregnation solution and the support is, optionally after aging, dried. It is also possible to employ an excess of solution, in which case the volume of this solution is greater than the porous volume of the zeolite. Here, the zeolite is mixed with the impregnation solution and stirred for a sufficiently long time. It is also possible to spray the zeolite with a solution of salts of at least one active component. Other methods known to those skilled in the art, e.g. precipitation of at least one active component on the zeolite, spraying-on of a solution comprising a compound of the at least one active component, sol impregnation, etc, are also possible.

According to the invention, the at least one active component can also be applied by a dry chemical route, for example by depositing gaseous metal carbonyls such as $Mo(CO)_6$ from the gas phase onto the zeolite at elevated temperatures.

After application of at least one active metal to the particulate fluidized-bed catalyst obtained from step IV, the catalyst is optionally dried at from about 80 to 130° C. for usually from 4 to 20 hours under reduced pressure or in air.

The catalyst particles are optionally calcined in step (V) at temperatures which are generally in the range from 350° C. to 750° C., preferably from 350° C. to 650° C. and particularly preferably from 400° C. to 600° C.

The present invention further provides a fluidized-bed catalyst which can be produced by the process of the invention comprising the above-described steps I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying, and
IV. calcination of the spray-dried fluidized-bed catalyst obtained from step III, where steps Ia and i) to iv) as described above can optionally also be carried out.

According to the invention, preference is given to a fluidized-bed catalyst which can be produced by the process of the invention comprising the above-described steps I. provision of an aqueous suspension comprising zeolite particles,
II. addition of a silicone resin mixture comprising one or more hydrolyzable silicone resin precondensates and mixing of the aqueous suspension and the silicone resin mixture,
III. spray drying of the mixture obtained from step II, with the mixture being homogenized before spray drying,
IV. calcination of the spray-dried fluidized-bed catalyst obtained from step III, and
V. application of at least one active metal to the fluidized-bed catalyst obtained from step IV and optionally subsequent drying and/or optionally calcination of the particulate fluidized-bed catalyst, where steps Ia and i) to iv) as described above can optionally be carried out in addition.

The fluidized-bed catalyst of the invention preferably comprises from 5 to 40% by weight, more preferably from 10 to 25% by weight, of silicon dioxide and from 60 to 95% by weight of zeolite, more preferably from 75 to 90% by weight of zeolite, based on the total weight of the particulate fluidized-bed catalyst.

The catalyst of the invention particularly preferably comprises from 0.1 to 20% by weight of active metal selected from the group consisting of Mo, W, Re, Ir, Ru, Rh, Pt, Pd and mixtures thereof, preferably selected from the group consisting of Mo, W, Re and mixtures thereof, based on the total weight of the particulate fluidized-bed catalyst.

In a further preferred embodiment, the particulate fluidized-bed catalyst comprises, in addition to at least one active metal, at least one further metal selected from the group consisting of W, Cu, Ni, Fe, Co, Mn, Cr, Nb, Ta, Zr, V, Zn, Ga and mixtures thereof, preferably selected from the group consisting of W, Cu, Ni, Fe and mixtures thereof.

The average particle size of the fluidized-bed catalyst of the invention is from 10 to 200 µm, preferably from 20 to 180 µm and particularly preferably from 50 to 150 µm, determined using a Malvern instrument (Malvern Mastersizer 2000).

The present invention further provides for the use of the fluidized-bed catalyst of the invention comprising at least from 0.1 to 20% by weight of active metal selected from the group consisting of Mo, W, Re, Ir, Ru, Rh, Pt, Pd and mixtures thereof, preferably selected from the group consisting of Mo, W, Re and mixtures thereof, and optionally at least one further metal selected from the group consisting of W, Cu, Ni, Fe, Co, Mn, Cr, Nb, Ta, Zr, V, Zn, Ga and mixtures thereof, preferably selected from the group consisting of W, Cu, Ni, Fe and mixtures thereof, for the nonoxidative dehydroaromatization of $C_1$-$C_4$-aliphatics.

For the purposes of the present invention, nonoxidative conditions means that the concentration of oxidants such as oxygen or nitrogen oxides in the feedstream E is below 5% by weight, preferably below 1% by weight, particularly preferably below 0.1% by weight. The mixture is very particularly preferably free of oxygen. Particular preference is likewise given to a concentration of oxidants in the mixture E which is equal to or lower than the concentration of oxidants in the source from which the $C_1$-$C_4$-aliphatics originate.

The present invention further provides a process for the dehydroaromatization of a feedstream comprising $C_1$-$C_4$-aliphatics by reaction of the feedstream E in the presence of the above-described fluidized-bed catalyst.

The feedstream E preferably comprises at least one aliphatic hydrocarbon having from 1 to 4 carbon atoms. Such aliphatics include, for example, methane, ethane, propane, n-butane, i-butane, ethene, propene, 1- and 2-butene, isobutene etc. In one embodiment of the invention, the feedstream E comprises at least 50 mol %, preferably at least 60 mol %, particularly preferably at least 70 mol %, especially preferably at least 80 mol %, in particular at least 90 mol %, of $C_1$-$C_4$-aliphatics.

Among the aliphatics, particular preference is given to using the saturated alkanes, and the feedstream E then preferably comprises at least 50 mol %, preferably at least 60 mol %, particularly preferably at least 70 mol %, especially preferably at least 80 mol %, in particular at least 90 mol %, of alkanes having from 1 to 4 carbon atoms.

Among the alkanes, preference is given to methane and ethane, in particular methane. In this embodiment of the present invention, the feedstream E preferably comprises at least 50 mol %, preferably at least 60 mol %, particularly preferably at least 70 mol %, especially preferably at least 80 mol %, in particular at least 90 mol %, of methane.

Natural gas is preferably used as source of the $C_1$-$C_4$-aliphatics. The typical composition of natural gas is: from 75 to 99 mol % of methane, from 0.01 to 15 mol % of ethane, from 0.01 to 10 mol % of propane, up to 6 mol % of butane and higher hydrocarbons, up to 30 mol % of carbon dioxide, up to 30 mol % of hydrogen sulfide, up to 15 mol % of nitrogen and up to 5 mol % of helium. The natural gas can be purified and enriched before use in the process according to the invention by methods known to the person skilled in the art. Part of purification is for example the removal of hydrogen sulfide or carbon dioxide which may be present in the natural gas and further compounds which are undesirable in the subsequent process.

The $C_1$-$C_4$-aliphatics comprised in the feedstream E can also originate from other sources, for example they can have been obtained in refining of petroleum. The $C_1$-$C_4$-aliphatics can also have been produced regeneratively (e.g. biogas) or synthetically (e.g. Fischer-Tropsch synthesis).

If biogas is used as $C_1$-$C_4$-aliphatics source, the feedstream E can additionally comprise ammonia, traces of lower alcohols and further components typical of biogas.

In a further embodiment of the process of the invention, LPG (liquefied petroleum gas) can be used as feedstream E. In a further embodiment of the process of the invention, LNG (liquefied natural gas) can be used as feedstream E.

Hydrogen, steam, carbon monoxide, carbon dioxide, nitrogen and one or more noble gases can additionally be mixed into the feedstream E.

According to the invention, the dehydroaromatization of $C_1$-$C_4$-aliphatics is carried out in the presence of the above-described, catalyst of the invention at temperatures of from 400 to 1000° C., preferably from 500 to 900° C., particularly preferably from 600 to 800° C., in particular from 700 to 750° C., at a pressure of from 0.5 to 100 bar, preferably from 1 to 50 bar, particularly preferably from 1 to 30 bar, in particular from 1 to 10 bar. According to the present invention, the reaction is carried out at a GHSV (gas hourly space velocity) of from 100 to 10 000 $h^{-1}$, preferably from 200 to 3000 $h^{-1}$.

Of course, the catalysts used according to the invention in the dehydroaromatization can be regenerated by customary methods known to those skilled in the art when the activity decreases. Regeneration of the catalyst by means of hydrogen is particularly preferred according to the present invention. This can be effected, for example, by addition of hydrogen to the feedstream E. The ratio of hydrogen stream to feedstream E is usually in the range from 1:1000 to 1:1, preferably from 1:500 to 1:5. However, it is also possible to pass feedstream E and hydrogen alternately over the catalyst.

The catalysts of the invention which comprise at least one further element selected from the group consisting of W, Cu, Ni, Fe and mixtures thereof can be regenerated well by means of hydrogen.

The dehydroaromatization of $C_1$-$C_4$ aliphatics can in principle be carried out in all types of reactor known from the prior art. A suitable form of reactor is a fixed-bed, tube or cell-and-tube reactor. In these, the catalyst is present as a fixed bed in a reaction tube or in a bundle of reaction tubes. The catalysts of the invention can likewise be used as fluidized bed or moving bed in the appropriate types of reactor suitable for this purpose and the dehydroaromatization process of the invention can be carried out using the catalysts present in this form.

The invention is illustrated below with the aid of examples.

EXAMPLES

A Production of the Particulate Fluidized-Bed Catalyst
A1. Ammonium Exchange

A commercially available H-ZSM-5 zeolite from Zeochem was used as zeolite. Since the zeolite was already present in the H form, only one ammonium exchange was carried out.

19 kg of the H-ZSM-5 zeolite were added to a solution of 19 kg of ammonium nitrate in 170 l of water and stirred at 80° C. for 2 hours. After cooling, the suspension was filtered in a filter press and washed with water. The filtercake was subsequently dried overnight at 120° C.

A2. Milling of the Zeolite

The zeolite from A1 was milled by wet milling in a stirred mill (Bühler DCP SF 12) as 50% strength suspension of zeolite in water until the $D_{90}$ was <3 µm.

A3. Addition of the Binder and Mixing

One part of the aqueous zeolite suspension from A2 was in each case stirred and the appropriate amount of the respective binder was slowly added. The respective proportions by weight of zeolite and silica in the individual catalysts are shown in the tables, based on the total weight of zeolite and $SiO_2$ after calcination of the spray-dried catalyst particles. The mixture was mixed for 1 hour.

A4. Spray Drying

Spray drying was carried out using the suspension from A3 in a commercial atomization dryer from Niro using nitrogen as atomizer gas. Two different nozzles, one a "two-fluid nozzle" and a "pressure nozzle", were used. The temperature during drying was in the range from 100 to 280° C.

A5. Calcination

The spray-dried catalyst particles from A4 were subsequently after-dried overnight at 120° C. and subsequently calcined at 500° C., unless indicated otherwise, for 4 hours in an air atmosphere.

A6. Application of Mo 1 kg of the particulate catalyst from A5 was impregnated with an aqueous solution of ammonium heptamolybdate (>99%, Aldrich) so that the amount of molybdenum on the catalyst particles was 6% by weight, based on the total weight of the catalyst, with the amount of water necessary for pore impregnation of the catalyst particles being used. The catalyst was mixed for 1 hour.

A7. Drying and Calcination

The catalyst from A6 was subsequently dried overnight at 120° C. and calcined at 500° C. for 4 hours in an air atmosphere. In the case of the catalysts of examples 1 to 10, steps A1 to A5 were carried out, and in the case of the catalysts of examples 11 and 12, steps A1 to A7 were carried out.

Example 1

According to the Invention

A methylmethoxysiloxane marketed under the trade name Silres® MSE 100 by Wacker Silikon was used as silicone resin precondensate for the binder. Silres® MSE 100 comprises from 60 to 100% by weight of polymethoxymethylsiloxane/methylsilsesqisiloxane, from 1 to 5% by weight of toluene and varying amounts of methanol. Spray drying was carried out using a two-fluid nozzle.

Examples 2 and 3

Not According to the Invention

Colloidal silica I, a 40% strength suspension in water (Ludox® AS 40, Aldrich), is used as binder. Spray drying was carried out using a two-fluid nozzle.

Example 4

Not According to the Invention

Colloidal silica II, a dispersion of amorphous, colloidal silica particles in water, is used as binder. The concentration of $SiO_2$ is 30% by weight (Nalco® DVSZN006, Nalco Company). Spray drying was carried out using a two-fluid nozzle.

Example 5

Not According to the Invention

The aqueous silica suspension I (AERODISP® WS1836, Evonik) having an $SiO_2$ content of 34% by weight and an average aggregate size of 0.3 µm was used as binder. Spray drying was carried out using a two-fluid nozzle.

Example 6

Not According to the Invention

The silica suspension II, an aqueous suspension of pyrogenic silica marketed under the trade name AEROSIL® 200 (Evonik), was used as binder. Spray drying was carried out using a two-fluid nozzle.

Example 7

According to the Invention

The silicone resin precondensate from example 1 was used as binder. Spray drying was carried out using a pressure nozzle.

Example 8

According to the Invention

The silicone resin precondensate from example 1 was used as binder. Spray drying was carried out using a pressure nozzle.

Example 9

Not According to the Invention

The silicone resin precondensate from example 1 was used as binder. A pressure nozzle was used for spray drying. In contrast to example 8, the mixture of aqueous zeolite suspension and silicone resin precondensate was allowed to stand after mixing and not homogenized before spray drying. The organic phase was separated off before spray drying.

Example 10

According to the Invention

The procedure of example 8 was used for producing the catalyst particles, but spray drying and after-drying were followed by calcination overnight at 800° C. instead of 500° C. as in example 8.

Example 11

Not According to the Invention

Mo was applied as per A6 and A7 to the catalyst particles from example 4.

Example 12

According to the Invention

Mo was applied as per A6 and A7 to the catalyst particles from example 1.

Example 13

According to the Invention

The procedure of example 1 was repeated with the amount of methylmethoxysiloxane being selected so that the amount of zeolite in the finished catalyst was 71% by weight.

Example 14

According to the Invention

A mixture of the silicone resin precondensate from example 1 (polymethoxysiloxane) and the colloidal silica II from example 4 was used as binder. The two components were mixed at 60° C. before addition to the zeolite. 1000 g of binder (amount of solids in the binder) having a weight ratio of polymethoxysiloxane:colloidal silica II of 0.25:1 (corresponds to 20% by weight of polymethoxysiloxane to 80% by weight of colloidal silica II) were used per 2500 g of zeolite. The temperature at the inlet of the spray dryer was 280° C.

Example 15

According to the Invention

The procedure of example 13 was repeated using a weight ratio of polymethoxysiloxane to colloidal silica II of 1:1 (corresponds to 50% by weight of polymethoxysiloxane to 50% by weight of colloidal silica II).

Example 16

According to the Invention

The procedure of example 14 was repeated with the calcination being carried out at 800° C.

Example 17

According to the Invention

The procedure of example 13 was repeated using a weight ratio of polymethoxysiloxane to colloidal silica II of 2.3:1 (corresponds to 70% by weight of polymethoxysiloxane to 30% by weight of colloidal silica II).

Example 18

According to the Invention

The procedure of example 13 was repeated using a weight ratio of polymethoxysiloxane to colloidal silica II of 4:1 (corresponds to 80% by weight of polymethoxysiloxane to 20% by weight of colloidal silica II).

Example 19

According to the Invention

The procedure of example 17 was repeated with the calcination being carried out at 800° C.

Example 20

According to the Invention

The procedure of example 17 was repeated with the temperature at the inlet of the spray dryer being 155° C.

Example 21

According to the Invention

The procedure of example 13 was repeated using a weight ratio of polymethoxysiloxane to colloidal silica II of 9:1 (corresponds to 90% by weight of polymethoxysiloxane to 10% by weight of colloidal silica II).

Example 22

According to the Invention)

6% by weight of Mo was applied to the catalyst from example 18 in accordance with procedures A6 and A7, with the impregnation with the ammonium heptamolybdate and drying at 120° C. being followed by a second impregnation with nickel nitrate (<99%, Aldrich) so that the amount of Ni on the catalyst particles was 0.5% by weight, based on the total weight of the catalyst. The catalyst was then again dried at 120° C. and subsequently calcined at 500° C. for 5 hours.

B Determination of the Degrees of Abrasion

The measurement of the degrees of abrasion was carried out in a jet abrasion apparatus using a method analogous to ASTM D5757.

The abrasion test simulates the mechanical stresses to which fluidized material (e.g. a catalyst) is subjected in a gas/solid fluidized bed and gives a degree of abrasion and a proportion of fines which describe the strength behavior. The abrasion apparatus comprises a nozzle plate (holes diameter=0.5 mm) which is connected in a gastight and solids-tight manner to a glass tube. Above the glass tube, a steel tube having a conical widening is attached, likewise in a gastight and solids-tight manner. The apparatus is connected to the 4 bar compressed air network. A reducing valve decreases the pressure to 2 bar absolute upstream of the apparatus. 60.0 g of catalyst are introduced into the apparatus. The flow rate of compressed air for carrying out the experiment is 350 l/h. The apparatus itself is operated under atmospheric conditions (1 bar, 20° C.). The particles are abraded or broken up by particle/particle and particle/wall impacts as a result of the high gas velocity at the nozzle. The discharged solid goes via a pipe dent into a filter paper thimble (pore opening 10-15 μm). The collected solid (particles<20 μm) is weighed after one hour (defined as proportion of fines) and after 5 hours (defined as abrasion). The degree of abrasion is defined as the solid discharged per hour between the first and sixth hours, based on the mass of solid weighed in. [Degree of abrasion [g/kg h]=discharge in 5 h after 1 h prestressing/(5*mass weighed in)].

The degrees of abrasion shown below were determined before application of the Mo.

The results of the measurement of the degrees of abrasion for the catalysts from examples 1 to 6 are summarized in table 1. It can clearly be seen that the catalyst particles of example 1 produced according to the invention using the silicone resin precondensate as binder display the best abrasion resistance.

TABLE 1

| Example | Binder | Zeolite (% by weight) | Degree of abrasion (g/kgh) |
|---|---|---|---|
| 1 | Polymethoxysiloxane (according to the invention) | 78 | 13 |
| 2 | Colloidal silica I (not according to the invention) | 71 | 68 |
| 3 | Colloidal silica I (not according to the invention) | 62 | 42 |
| 4 | Colloidal silica II (not according to the invention) | 71 | 29 |
| 5 | Silica suspension I (not according to the invention) | 71 | too high, outside the measurement range |
| 6 | Silica suspension II (not according to the invention) | 71 | 31 |

The influence of the binder concentration is shown by examples 7 and 8 in table 2: a smaller amount of binder gives a better degree of abrasion. Furthermore, table 2 gives the results of the abrasion test for example 9 in which only the aqueous phase was fed to spray drying after the organic phase had been separated off. This example shows that omission of the homogenization of the mixture obtained in step III before spray drying leads to catalyst particles having significantly poorer degrees of abrasion.

TABLE 2

| Example | Binder | Zeolite (% by weight) | Degree of abrasion (g/kgn) |
|---|---|---|---|
| 7 | Polymethoxysiloxane (according to the invention) | 83 | 10 |
| 8 | Polymethoxysiloxane (according to the invention) | 78 | 21 |
| 9 | Polymethoxysiloxane, with removal of the organic phase (not according to the invention) | 78 | 56 |

Table 3 reports the results of the measurement of the degrees of abrasion for the catalysts from examples 8 and 10 and also for the catalysts from examples 13 to 20. A higher calcination temperature leads to catalysts having improved degrees of abrasion.

TABLE 3

| Example | Binder | % by weight of zeolite | Calcination (° C.) | Degree of abrasion (g/kgh) |
|---|---|---|---|---|
| 8 | Polymethoxysiloxane (according to the invention) | 78 | 500 | 21 |
| 10 | Polymethoxysiloxane (according to the invention) | 78 | 800 | 6 |
| 13 | Polymethoxysiloxane (according to the invention) | 71 | 500 | 27 |
| 14 | Polymethoxysiloxane: colloidal silica II (according to the invention) 0.25:1 | | 500 | 12 |
| 15 | Polymethoxysiloxane: colloidal silica II (according to the invention) 1:1 | | 500 | 19 |
| 16 | Polymethoxysiloxane: colloidal silica II (according to the invention) 1:1 | | 800 | 18 |
| 17 | Polymethoxysiloxane: colloidal silica II (according to the invention) 2.3:1 | | 500 | 15 |
| 18 | Polymethoxysiloxane: colloidal silica II (according to the invention) 4:1 | 71 | 500 | 7 |
| 19 | Polymethoxysiloxane: colloidal silica II (according to the invention) 4:1 | 71 | 800 | 5 |
| 20 | Polymethoxysiloxane: colloidal silica II (according to the invention) 4:1 | 71 | 500 | 6 |
| 21 | Polymethoxysiloxane: colloidal silica II (according to the invention) 9:1 | | 500 | 23 |

The use according to the invention of a silicone resin precondensate leads, particularly when colloidal silica conventionally known as binder is simultaneously used, to significantly improved degrees of abrasion of the finished shaped catalyst body. This can be seen, in particular, when examples 13 to 20 are compared with example 4. Particularly good results are obtained using a mixture of silicone resin precondensate and colloidal silica in a weight ratio of 4:1.

C N$_2$ Absorption Measurement

The nitrogen absorption isotherms were determined for the catalysts from examples 1 (according to the invention) and 4 (not according to the invention). The measurements were carried out using the Quantachrom Autosorb 6b: nitrogen sorption at −196° C., outgassing temp.=200° C., outgassing time=14 h, determination of the micropore volume by the DR method.

The measured values are shown in table 4. The catalyst from example 1 shows a nitrogen absorption isotherm corresponding to class I (classification in accordance with IUPAC), while the catalyst from example 4 shows a nitrogen absorption isotherm corresponding to class IV. This indicates that the catalyst from example 4 has more micropores having a pore size in the nanometer range (pore diameter<2 nm) than the catalyst according to the invention from example 1 which has more pores in the mesopore and macropore range (pore diameter>2 nm).

TABLE 4

| | BET (m$^2$/g) | Total pore volume (cm$^3$/g) | Micropore volume (cm$^3$/g) | Mesopore and macropore volume (cm$^3$/g) |
|---|---|---|---|---|
| Example 1 | 285 | 0.29 | 0.12 | 0.17 |
| Example 4 | 324 | 0.28 | 0.15 | 0.13 |

D Nonoxidative Dehydroaromatization of Methane

The experiments were carried out using 100 g of the respective catalyst in a fluidized-bed reactor. Before the reaction, the catalysts were carburized by passing a stream of methane through the reactor at a flow rate of 100 standard l/h until the reaction temperature had been reached. The flow rate was calculated for STP. The reaction began immediately thereafter at 700° C. and 2.5 bar and was carried out using a mixture of $CH_4$/He (90:10) at a flow of 20 standard l/h. The catalysts were regenerated at regular intervals by passing hydrogen through the reactor at 4 bar and 750° C. for 5 hours. A reaction cycle took 10 hours.

The results for the catalyst according to the invention from example 1 and the noninventive catalyst from example 4 are summarized in table 5. $X_{CH4}$ is the proportion of methane reacted based on the total amount of methane used in %; $S_{C6H6}$ is the proportion of benzene based on the amount of methane reacted, in %. The reported Mo concentration is based on the total weight of the catalyst including Mo.

TABLE 5

| Example | Catalyst from example | % by weight of Mo | 3rd reaction cycle, measured at 6 h | | 6th reaction cycle, measured at 6 h | | 8th and 10th reaction cycle, measured at 6 h | |
|---|---|---|---|---|---|---|---|---|
| | | | $X_{CH4}$ (%) | $S_{C6H6}$ (%) | $X_{CH4}$ (%) | $S_{C6H6}$ (%) | $X_{CH4}$ (%) | $S_{C6H6}$ (%) |
| 11 | 4 (not according to the invention) | 5.9 | 8.9 | 59 | 8.6 | 52 | | |
| 12 | 1 (according to the invention) | 6.0 | 8.4 | 65 | 8.4 | 70 | 7.9 (10th) | 69 (10th) |
| 21 | 21 (according to the invention) | 6.0 + 0.5 % by weight of Ni | 10.8 | 67 | 9.0 | 75 | 8.9 (8th) | 75 (8th) |

The measurement for the noninventive catalyst (example 11) was stopped after the 6th cycle since selectivities of only 50% are not of interest for industrial use. It can clearly be seen that the catalysts comprising, according to the invention, silicone resin precondensates as binder display a better selectivity to benzene at comparable methane conversions.

The invention claimed is:

1. A particulate fluidized-bed catalyst, obtained by a process comprising:
   (I) forming an aqueous suspension comprising zeolite particles;
   (II) adding a silicone resin mixture comprising a hydrolyzable silicone resin precondensate to the aqueous suspension and mixing the aqueous suspension and the silicone resin mixture, to obtain an intermediate mixture;
   (III) homogenizing the intermediate mixture and then spray drying the intermediate mixture, to obtain a spray-dried fluidized-bed catalyst; and
   (IV) calcinating the spray-dried fluidized-bed catalyst, to obtain a calcinated fluidized-bed catalyst comprising a zeolite having at least one structure selected from the group consisting of a pentasil structure and a MWW structure.

2. The particulate fluidized-bed catalyst according to claim 1, comprising, based on a total weight of the fluidized-bed catalyst:
   from 5 to 40% by weight of silicon dioxide; and
   from 60 to 95% by weight of zeolite.

3. The particulate fluidized-bed catalyst according to claim 1, comprising:
   from 0.1 to 20% by weight of an active metal selected from the group consisting of Mo, W, Re, Ir, Ru, Rh, Pt, Pd and mixtures thereof, based on the total weight of the particulate fluidized-bed catalyst.

4. The particulate fluidized-bed catalyst according to claim 3, further comprising:
   at least one metal selected from the group consisting of W, Cu, Ni, Fe, Co, Mn, Cr, Nb, Ta, Zr, V, Zn and Ga.

5. A process for dehydroaromatizing a $C_1$-$C_4$-aliphatic, the process comprising:
   reacting a feedstream comprising a $C_1$-$C_4$-aliphatic and less than 5% by weight of oxidants, based on a total weight of the feedstream, in the presence of a fluidized-bed catalyst according to claim 3.

6. A process for dehydroaromatizing a $C_1$-$C_4$-alipahtic, the process comprising:
   reacting a feedstream E comprising a $C_1$-$C_4$-alipahtic in the presence of a fluidized-bed catalyst according to claim 4.

7. The particulate fluidized-bed catalyst according to claim 2, wherein the zeolite has at least one structure selected from the group consisting of a pentasil structure and a MWW structure.

8. The particulate fluidized-bed catalyst according to claim 1, wherein at least one further Si-comprising binder selected from the group consisting of silica, silica suspensions and silica sols is further added to the aqueous suspension during the adding (II).

9. The particulate fluidized-bed catalyst according to claim 8, wherein the zeolite particles are H-ZSM-5.

* * * * *